US010948473B2

(12) United States Patent
Jarvis (10) Patent No.: US 10,948,473 B2
(45) Date of Patent: Mar. 16, 2021

(54) METHOD OF AND APPARATUSES FOR ASSESSING FAT IN DAIRY PROCESSING (71) Applicant: Arla Foods Limited, Leeds (GB)

(72) Inventor: Ian Jarvis, Lockerbie (GB)

(73) Assignee: Arla Foods Limited, Leeds (GB)

( * ) Notice: Subject to any disclaimer, the term of this patent is extended or adjusted under 35 U.S.C. 154(b) by 75 days.

(21) Appl. No.: 16/060,436

(22) PCT Filed: Dec. 8, 2016

(86) PCT No.: PCT/GB2016/053862
§ 371 (c)(1),
(2) Date: Jun. 8, 2018

(87) PCT Pub. No.: WO2017/098246
PCT Pub. Date: Jun. 15, 2017

(65) Prior Publication Data
US 2019/0025272 A1    Jan. 24, 2019

(30) Foreign Application Priority Data
Dec. 9, 2015  (GB) ..................... 1521686

(51) Int. Cl.
*G01N 33/06* (2006.01)
*G01N 21/53* (2006.01)
(Continued)

(52) U.S. Cl.
CPC .......... *G01N 33/06* (2013.01); *G01N 21/532* (2013.01); *A23C 13/12* (2013.01); *A23C 15/06* (2013.01);
(Continued)

(58) Field of Classification Search
CPC .......... A23C 13/12; A23C 15/06; A23C 15/16; A23C 19/02; A23C 21/00; G01N 33/06; G01N 33/04
See application file for complete search history.

(56) References Cited

U.S. PATENT DOCUMENTS 2,264,665 A * 12/1941 Hall ..................... A23C 9/1508
426/417
2,567,898 A *  9/1951 Staaff ..................... A23C 13/12
426/231
(Continued)

FOREIGN PATENT DOCUMENTS

SU        556380 A1 *  5/1977
SU        564599 A1 * 11/1977
(Continued)

OTHER PUBLICATIONS

Castillo et al., "Optical sensor technology for measuring whey fat concentration in cheese making", Journal of Food Engineering, No. 71, pp. 354-360, Dec. 16, 2004. (Year: 2004).*
(Continued)

*Primary Examiner* — David A. Rogers
(74) *Attorney, Agent, or Firm* — Renner, Otto, Boisselle & Sklar, LLP (57) ABSTRACT A method of and apparatus (18) are described for assessing fat in whey in the making of a dairy product in accordance with a dairy product recipe. The method comprises the steps of: a. using one or more optical sensors (61, 62, 63, 64) to sense at least one stream (22, 24, 27, 29) of whey separated from curd in dairy product making apparatus (18) and generate one or more signals indicative of the degree of occlusion of the stream (22, 24, 27, 29) of whey; b. converting or processing one or more said signals as a measure of the specific mass of fat lost from curd in a dairy product making plant (18) in the stream of whey; c. assessing
(Continued)

whether the value of specific mass of fat lost obtained in Step b lies within or outside a predetermined fat loss range; and d. if the said value of specific mass of fat lost is outside the predetermined range, adjusting the recipe so that the value of specific mass of fat lost lies within the predetermined range.

23 Claims, 4 Drawing Sheets

(51) Int. Cl.
   A23C 19/02   (2006.01)
   A23C 15/06   (2006.01)
   A23C 21/00   (2006.01)
   A23C 13/12   (2006.01)
   A23C 15/16   (2006.01)
   G01N 21/47   (2006.01)

(52) U.S. Cl.
   CPC ............. *A23C 15/16* (2013.01); *A23C 19/02* (2013.01); *A23C 21/00* (2013.01); *G01N 2021/4726* (2013.01); *G01N 2201/0221* (2013.01)

(56) References Cited

U.S. PATENT DOCUMENTS

| | | | | |
|---|---|---|---|---|
| 2,752,815 A * | 7/1956 | Batchelor | ............... | G01N 33/04 356/36 |
| 3,161,768 A * | 12/1964 | Goulden | ................ | G01N 33/04 250/339.12 |
| 3,560,219 A * | 2/1971 | Attebery | ................ | A23C 21/00 426/583 |
| 3,829,584 A * | 8/1974 | Seiberling | ................ | A01J 11/10 426/231 |
| 3,972,625 A * | 8/1976 | Takahasi | ............... | G01N 21/534 356/435 |
| 3,983,257 A * | 9/1976 | Malmberg | ................ | A01J 11/10 426/231 |
| 4,017,643 A * | 4/1977 | Lester | .................. | A23C 9/1508 426/231 |
| 4,144,804 A * | 3/1979 | O'Keefe | .................. | A01J 11/10 137/110 |
| 4,247,773 A * | 1/1981 | Nexo | ..................... | G01N 33/06 250/339.12 |
| 4,447,725 A * | 5/1984 | Biggs | ..................... | G01N 21/31 250/339.12 |
| 4,521,433 A * | 6/1985 | Linklater | ............... | A23C 19/02 426/36 |
| 4,841,157 A * | 6/1989 | Downing, Jr. | ......... | G01N 21/53 250/574 |
| 5,009,794 A * | 4/1991 | Wynn | ................... | A23C 9/1508 137/93 |
| 5,137,738 A * | 8/1992 | Wynn | ................... | A23C 9/1508 210/745 |
| 5,928,702 A * | 7/1999 | Lidman | ................ | A23C 9/1508 426/580 |
| 5,955,128 A | 9/1999 | Bayevsky et al. | | |
| 6,147,502 A * | 11/2000 | Fryer | ..................... | G01N 22/00 324/637 |
| 6,874,355 B2 * | 4/2005 | Kornfeldt | .............. | C12M 29/18 73/32 A |
| 6,916,499 B1 * | 7/2005 | Landon | .................. | A23C 15/16 426/491 |
| 7,880,881 B2 * | 2/2011 | Everard | .................... | G01J 3/02 356/402 |
| 2014/0130745 A1 * | 5/2014 | Van Halsema | .... | G06K 9/00362 119/14.08 |

FOREIGN PATENT DOCUMENTS

SU         611599 A1 *  5/1978
WO   WO-2009065988 A1 *  5/2009   ........... G01N 21/359

OTHER PUBLICATIONS

"Butter Production—Technology and Process", SPX Corporation, Jul. 2012. (Year: 2012).*
Colette Fagan et al., "Effect of Cutting Time, Temperature, and Calcium on Curd Moisture, Whey Fat Losses, and Curd Yield by Response Surface Methodology", Journal of Dairy Science, vol. 90, No. 10, 2007. (Year: 2007).*
R. B. Maxcy et al., "Improving Curd-Forming Properties of Homogenized Milk", Journal of Dairy Science, vol. 38, 1955. (Year: 1955).*
Elisângela Serenato Madalozzo et al., "Determination of Fat, Protein and Moisture in Ricotta Cheese by Near Infrared Spectroscopy and Multivariate Calibration", Journal of Food Science Technology, vol. 52, No. 3, Aug. 16, 2013. (Year: 2013).*
M. J. Mateo et al., "Effect of Milk Fat Concentration and Gel Firmness on Syneresis During Curd Stirring in Cheese-Making", International Dairy Journal , vol. 19, 2009. (Year: 2009).*
C. Cipolat-Gotet et al., "Factors Affecting Variation of Different Measures of Cheese Yield and Milk Nutrient Recovery From an Individual Model Cheese-Manufacturing Process", Journal of Dairy Science, vol. 96, 2013. (Year: 2013).*
Sheila B. McCarron et al., "An Evaluation of Fat Recovery into Cheddar Cheese in a Modern Creamery", Irish Journal of Food Science and Technology, vol. 14, No. 1, 1990. (Year: 1990).*
Pranay Jain et al., "Light Scattering and Transmission Measurement Using Digital Imaging for Online Analysis of Constituents in Milk", Proceedings of Society of Photographic Instrumentation Engineers, vol. 9525, Jun. 22, 2015. (Year: 2015).*
Anonymous: "Equipping a cheese dairy with inline spectroscopic analysis systems", , Feb. 2015 (Feb. 2015), XP055351929, Retrieved from the Internet: URL:http://krohne.com/fileadmin/content/files-2/ctry_global/application_reports/food/AP _No421_EN_Food.pdf.
International Search Report and Written Opinion dated Mar. 17, 2017 for PCT/GB2016/053862.

* cited by examiner

METHOD OF AND APPARATUSES FOR ASSESSING FAT IN DAIRY PROCESSING

This application is a national phase of International Application No. PCT/GB2016/053862, filed Dec. 8, 2016, and published in the English language, which claims priority to United Kingdom Patent Application No. 1521686.4, filed Dec. 9, 2015, both of which are hereby incorporated herein by reference.

The invention relates to a method of and apparatuses for assessing fat in dairy processing, especially in the manufacture of cheese or yogurt.

As is well known a dairy product is a food or drink created from the milk of a lactating animal. The domesticated cow is by far the most popular source of milk used in dairy processing. It is however also known to produce dairy products from the milk of goats, sheep, yaks, horses, camels, domesticated buffaloes, and numerous other mammals.

Some dairy processes are based essentially on the separation of cream and skim milk (being the two primary components of whole milk) from one another. Separated cream may be packaged and sold for consumption in more or less its as-separated form; it may be used as an ingredient (e.g. in the production of ice-cream or semi-skim milk); or it may be further processed.

An example of the further processing of cream is the manufacture of butter, in which cream is churned until coagulation of fat globules gives rise to a semi-solid mass. The latter may be further processed into recognisable pack-sized units.

The manufacture of butter involves a form of syneresis, i.e. the separation of a liquid from a solid or semi-solid mass. In the case of butter-making the liquid is known as buttermilk.

Some other dairy processes are chemically more complicated than the agglomeration, described above, that results from the churning of cream to make butter. As examples in this regard one may consider the treatment of milk with bacteria and enzymes in the manufacture of cheese and yogurt.

Cheese- and yogurt-making are somewhat similar processes in which the bacteria and/or enzyme treatment of milk gives rise to the creation of a solid or semi-solid/soft mass.

In cheese- and yogurt-making processes syneresis is initiated by physical processes such as warming the partly-processed milk and/or cutting of the solid or semi-solid mass once the solid or semi-solid mass has formed. Such syneresis results in the production of one or more streams of liquid known as whey that are drained or otherwise removed from the solid curd that at the end of the syneresis process is packaged as cheese or yogurt.

The invention is applicable in dairy processes in which syneresis occurs, and in particular in the manufacture of cheese and yogurt. The invention also is applicable in the manufacture of butter.

One aspect of dairy processing is that the chemical compositions of the ingredients used, and in particular the milk that is the starting ingredient in dairy manufacturing, are highly variable. In this regard it is well known that the composition of cows' milk varies in accordance with numerous influences including e.g. the breed of cow from which the milk is collected, the variety of grass used for grazing, the amount of daylight to which the cows are exposed, the ages of the cows, the time of year, the altitude at which the cows are grazed, ambient temperatures and several other factors. Dairy companies may seek to minimise the effects of ingredient variability by blending milk from multiple sources. In some instances however this is impractical, is not desired or is prohibited by regulation; and even when milk blending is possible it does not completely solve the problem of ingredient variability.

Despite the problems caused by ingredient variability, modern supermarkets demand an extremely high degree of consistency in the products marketed as particular types or under particular brands. In response to this requirement those dairy manufacturers that produce products on any scale larger than the smallest must invest heavily in automated equipment. Notwithstanding this investment the variability of ingredients, and other variable factors in dairy processing, mean it is difficult for manufacturers to achieve the required product consistency.

A dairy production plant follows specific recipes for making various dairy products. Different types of dairy product naturally require different recipes. Recipes could include directions on how much to acidify the milk, how much starter culture to use, how much moisture to drive out, what additional moulds/bacteria to add and so on. The recipe for making one variety of a particular dairy product also differs from another variety of the same dairy product. Thus for example the recipe for making Gouda cheese is different from that for making Cheddar cheese.

A number of main stages of the dairy product making process are common to several types of dairy products. The process typically involves the removal of water from milk with a consequent multiple-fold concentration of the protein, fat, minerals and vitamins found in milk, resulting in the formation of a protein coagulum called curd that then shrinks to expel whey. Whey is the liquid remaining after milk has been curdled and strained.

Syneresis is as noted the separation process of the curd from the whey. It is important to manufacturers of dairy products to control the amount of fat in the curd.

It is known from U.S. Pat. No. 7,892,584 B2 to employ optical sensors to assess the stream of milk and the curds and whey mixture in a cheese-making process and use the resulting data in the determination of an optimum point for terminating syneresis.

A stated aim of the apparatus of U.S. Pat. No. 7,892,584 B2 is to improve the quality of cheese that is manufactured using automated dairy processing equipment.

According to an aspect of the invention, there is provided a method of assessing fat in whey in the making of a dairy product in accordance with a dairy product recipe, the method comprising the steps of:
  a. using one or more optical sensors to sense at least one stream of whey separated from curd in dairy product making apparatus and generate one or more signals indicative of the degree of occlusion of the stream of whey;
  b. converting or processing one or more said signals as a measure of the specific mass of fat lost from curd in a dairy product-making plant into the stream of whey;
  c. assessing whether the value of specific mass of fat lost obtained in Step b lies within or outside a predetermined fat loss range; and
  d. if the said value of specific mass of fat lost is outside the predetermined range, adjusting the recipe so that the value of specific mass of fat lost lies within the predetermined range.

Preferably the dairy product is cheese or yogurt. Alternatively the dairy product may be butter.

An influence on the consistency of dairy products such as cheese and yogurt that are nominally produced according to a given recipe is the amount of fat retained in the curd during syneresis. The inventor has surprisingly found that measuring the fat content of the whey stream(s) resulting from syneresis provides an effective basis for controlling curd fat content by way of recipe adjustments.

The method of the invention furthermore lends itself to being carried out in real time during the operation of automated dairy processing machinery. The method as a result is suitable for use in a variety of dairy processing installations, and especially large-scale dairy plant. Despite this, apparatus for carrying out the invention may conveniently be manufactured as e.g. a portable device that is easily installed in existing dairy plant equipment.

The process of real-time analysis of whey fat loss in the invention provides early warning to the operators of dairy product apparatus in the event of a vat containing partly-processed ingredients that are out of the fat content specification stipulated in a recipe. This allows consistent control over the manufacture of dairy products and enables pre-calculated and/or real-time recipe changes to be made as needed.

Advantageously the method includes the steps of:
e. using a plurality of optical sensors to sense a corresponding plurality of streams of whey separated from curd in dairy product making apparatus and generate a corresponding plurality of signals respectively indicative of the degree of occlusion of the streams of whey;
f. converting or processing the said signals as measures of the specific mass of fat lost from curd in the dairy product making plant in the streams of whey;
g. assessing whether the values of specific mass of fat lost obtained in Step f lie within or outside corresponding predetermined fat loss ranges; and
h. if one or more said values of specific mass of fat lost is outside a said corresponding predetermined range, adjusting the recipe so that each value of specific mass of fat lost lies within the corresponding predetermined range.

A corresponding plurality of optical sensors indicating the degree of occlusion of multiple streams of whey provides an accurate reading of whey fat loss in dairy plant in which such multiple streams are generated.

If the dairy product is cheese, it is preferable that the plurality of optical sensors sense streams of whey respectively at one or more of (i) an outlet of a draining table of the dairy product making apparatus; (ii) an outlet of a cheddaring tower of the dairy product making apparatus; (iii) an outlet of a salting table of the dairy product making apparatus; and (iv) an outlet of a block former of the dairy product making apparatus.

If the dairy product is yogurt, preferably one or more optical sensors sense one or more streams of whey at an outlet of a drainer or strainer of the dairy product making apparatus.

Thus the method of the invention as broadly defined is flexible and may be adapted for use in a variety of dairy product apparatuses.

It is an advantage if the or each stream of whey is/are generated from ingredients in a plurality of vats forming part of the dairy product making apparatus used sequentially to provide curds and whey.

As a result of this aspect of the invention it is possible to make recipe adjustments part-way through the processing of a large batch of ingredients contained in the plurality of vats. The provision of a sequentially treated series of vats is often the norm in large-scale dairy plant.

Preferably the step of generating one or more signals indicative of the degree of occlusion of the at least one stream of whey includes generating one or more signals indicative of the degree of turbidity of the at least one stream of whey.

Turbidity is straightforwardly assessed and measures the amount of light scattering caused by fat globules in the whey. This provides a good indication of the fat quantity in a whey stream.

It is advantageous if the step of using one or more optical sensors to sense at least one stream of whey includes directing a light beam from at least one light source through a said stream of whey towards an associated light detector that generates a current in dependence on the attenuation of the light in the stream of whey. Such an arrangement, which is known per se, advantageously may be readily configured for carrying out the sensing and signal generation steps of the invention.

Further advantageously the step of using one or more optical sensors to sense at least one stream of whey includes directing a respective light beam from each of at least two light sources through a said stream of whey towards respective associated light detectors that generate currents in dependence on the attenuation of the light in the stream of whey.

Preferably the two light sources are each intermittent and generate light one alternating with the other.

The alternating light principle design increases the sensitivity of optical sensors and improves the measurement reliability of fat in the whey stream.

It is an advantage of the method of the invention to display via a display device one or more indicia indicative of the value of specific fat loss.

The display provides a real-time indication to the operators of dairy apparatus that allows them to make any required adjustments to the manufacturing process and in particular the recipe used to make the dairy product.

Preferably the method of the invention generates, based on the measure of the specific fat loss in the or each stream of whey, one or more commands that effect adjustment of a parameter of dairy product making apparatus so that the value of specific fat loss lies within the predetermined range.

Advantageously the method of the invention includes storing a plurality of recipes in a relational or other database together with a plurality of predetermined ranges of specific fat loss value. The method further includes the steps of selecting a dairy product recipe; associating a said range of specific fat loss value with the selected recipe; and generating the or each said command based on the specific fat loss value associated with the recipe.

According to another aspect of the invention, there is provided a dairy product-making apparatus for carrying out a method of the invention as defined herein, the apparatus including one or more ingredient vats for containing dairy product making ingredients; at least one drainer having an outlet permitting removal of one or more streams of whey separated from curd; one or more optical sensors for sensing the one or more said streams of whey and generating one or more signals indicative of the degree of its occlusion; and a processor for converting one or more said signals as a measure of the specific mass of fat lost from curd in the stream of whey.

Preferably the drainer is a draining table as is used in cheese-making or is a strainer as is used in yogurt-making.

If the dairy product is cheese, it further is advantageous that the dairy product making apparatus additionally comprises a cheddaring tower, a salting table and a block former the mutual relationship of which permits the making of cheese.

It is preferable that the or each optical sensor includes at least two light sources that direct light through a said stream of whey and a corresponding number of respective associated light detectors that receive the light and generate currents in dependence on the attenuation of the light in the stream of whey.

Preferably the at least two light sources each generate light intermittently in alternation one with the other.

The foregoing apparatus features are particularly suited to practicing of the method of the invention.

According to a further aspect of the invention there is provided whey stream fat measuring apparatus comprising one or more sensors for sensing one or more streams of whey and generating one or more signals indicative of its degree of occlusion; and a processor for converting one or more said signals as a measure of the specific mass of fat lost from curd into the stream of whey.

Such apparatus may form part of dairy product-making apparatus as defined herein or may be constituted separately from the dairy product-making apparatus of the second aspect of the invention.

Preferably the or each optical sensor includes at least two light sources that direct light through a said stream of whey and a corresponding number of respective associated light detectors that receive the light and generate currents in dependence on the attenuation of the light in the stream of whey. Further preferably the at least two light sources each generate light intermittently in alternation one with the other. Thus the whey stream fat measuring apparatus may include several features of the dairy product-making apparatus of the invention.

Optionally the whey stream fat measuring apparatus may be humanly portable and releasably connectable to sense one or more streams of whey in dairy product-making apparatus. Advantageously when so configured the whey stream fat measuring apparatus may be contained within e.g. a packing case or similar container. Such a container may include e.g. a power source or a power cable connection for the sensor and processor; and on its exterior a display for displaying the results of the fat assessment. Alternatively the portable apparatus may include an on-board power source such as a compartment containing one or more electrical batteries.

A portable apparatus also may include a data port (that may be or a wired or wireless type). The data port may be used for interfacing with dairy processing plant to which the whey stream fat assessment apparatus is operatively connected; and may download recipe adjustment commands in accordance with the method of the invention.

Regardless of whether it is portable or not the whey stream fat measuring apparatus may be connected temporarily or permanently to measure fat in dairy plant whey streams.

This may be achieved e.g. by puncturing one or more whey stream conduits or by removing a removable plug in order to permit the insertion into the whey stream of the sensors of the apparatus.

According to a further aspect of the invention, there is provided a dairy product obtained from a process that includes a method of the invention as described above.

There now follows a description of preferred embodiments of the invention, by way of non-limiting example, with reference being made to the accompanying figures in which.

Embodiments of the invention will be described with reference to a method of and apparatus for assessing fat in whey in the making of cheese and yogurt.

The invention is however not limited to assessing fat in cheese and yogurt, and the method and apparatus can be used to assess fat in other dairy products.

The invention is also not limited to the following described process of making cheese.

Figure 1:
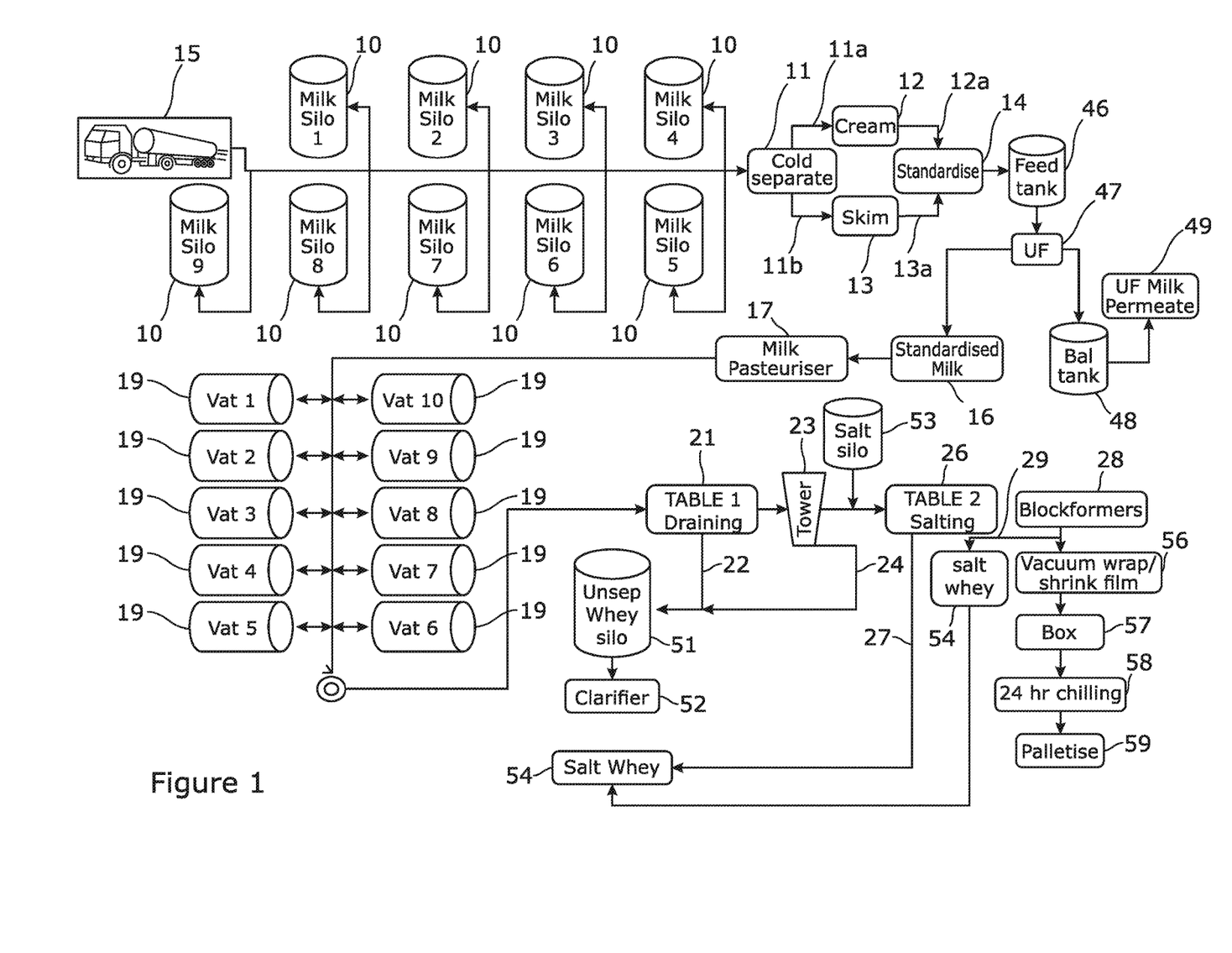
FIG. 1 is a schematic diagram of a dairy product-making apparatus, according to an embodiment of the invention, when constituted as a cheese-making plant.

FIG. 1 shows the flow of milk in a dairy production plant 18 according to the invention. In FIG. 1 milk is delivered typically by tanker 15 and initially stored in large silos 10 before being processed.

Generally the first step of cheese or yogurt production involves cold separation of raw milk fed via feed lines as illustrated to a separator 11. During the cold separation process, two streams are produced: a fat-rich stream 11$a$ consisting of cream 12 that can be used e.g. in the production of semi-skim milk, ice cream or butter; and a fat-depleted stream 11$b$ consisting of skim milk 13. Skim milk may be sold as a drink or ingredient, or it may be evaporated and possibly subsequently dried to produce various products. Cream and skim milk however also are used in per se known milk standardisation steps that are employed in cheese-making as described below.

Both streams of cream 12 and skim milk 13 therefore are used in the process of standardisation 14. Methods of standardising milk may include addition of concentrated non-fat milk solids, the addition of skim milk and the removal of cream.

One way, of several possible methods, illustrated in FIG. 1 in which cream and skim milk streams 12$a$, 13$a$ are mixed in chosen proportions is in a feed tank 46.

Optionally the standardised milk may be fed from the feed tank to ultrafiltration apparatus 47 from which filtered, standardised milk 16 is fed to an optional pasteuriser 17.

The ultrafiltration apparatus gives rise to a filtrate stream that is fed to a balancer tank 48. The balancer tank would not be present, or would not be used if present, if the ultrafiltration apparatus 47 is not present or is bypassed in the process flow. It is possible to draw off from the balancer tank 48, if used, an ultrafiltration milk permeate as signified by numeral 49. Ultrafiltration has the effect of concentrating principally the lactose content of the standardised milk 16.

The standardised milk 16 may or may not be required to be pasteurised. Pasteurisation can be performed as a batch or a continuous process in a pasteuriser 17. A typical pasteuriser consists of a temperature-controlled closed vat. The milk is pumped into the vat, heated to a pasteurisation temperature and held at that temperature for the appropriate time before being cooled. The cooled milk is then pumped out of the vat to the rest of the processing line of the dairy product making apparatus 18.

The cheese-making apparatus of FIG. 1 includes one or more ingredient vats 19 to which the standardised milk and additional ingredients are supplied for the purpose of curd formation. Although ten vats are illustrated, the invention is not limited to this number and there can be more or fewer than ten vats.

The majority of cheeses are made from (whole, low-fat or non-fat) heat-treated or pasteurised milk that is explained is typically subjected to a standardisation process before the cheese-making commences. The standardised milk in the ingredient vats 19 is firstly pre-treated, typically after the addition of a bacteria culture appropriate to the type of cheese. Most varieties of cheese cannot be made without the addition of a "starter" which is a culture of carefully selected lactic acid-producing bacteria. Adding of the starter culture converts lactose in the milk to lactic acid.

The resulting acidified milk is mixed with enzyme extracts such as rennet from calf stomachs, microbially produced enzymes or other similar enzymes. The enzyme activity causes the milk to coagulate to form a curd and whey mixture. Sweet whey is manufactured during the making of rennet types of hard cheese such as Cheddar or Gruyere. Acid whey (also known as "sour whey") is a by-product produced during the making of acid types of dairy products such as cottage cheese or strained yogurt. Salted whey is whey that has been salted and is typically obtained after the curd and whey mixture has been processed at a salting table or a block former.

As a result of processes such as those indicated above after a time a mixture of curds and whey exists in the vats 19. This mixture is in the preferred embodiment illustrated supplied to a draining table 21 that promotes the draining of whey from the curd following the commencement of syneresis as explained herein. The draining table 21 contains screens that allow the whey to drain via an outlet 22, but which trap the curd. In other embodiments of the invention however various other means of removing whey, including but not limited to perforated pipes, may be employed.

As a result of the syneresis process a stream of so-called unseparated whey is created. In the illustrated embodiment this is fed initially to an unseparated whey silo 51 which supplies whey to a clarifier 52. Following clarifying the whey may be further processed to be sold as e.g. a food ingredient, animal feed or dietary supplement.

From the draining table the partly drained curd is supplied to an optional cheddaring tower 23 where cheddaring occurs. This typically is a mild form of stretching in which the cheese curd is piled up and held at a moderate temperature so that it flows under the force of gravity. The curd is periodically turned to cause repeated flowing. The pH of the curd falls during this process until the level of acidity of the curd reaches a desired level. Whey continues to exude and flows via an outlet 24 of the cheddaring tower 23 to the unseparated whey silo 51. Cheddaring may not be required in e.g. soft cheese manufacturing, or it may be carried out in a different form than that described above.

The application of salt stored in a salt silo 53 to the curd causes more moisture to be expelled, both through an osmotic effect and a salting effect on the milk proteins. Salting typically is carried out at a salting table 26 to which the curd is transferred, and is specific for each cheese variety. Whey continues to drain from this part of the dairy product-making apparatus 18 via an outlet 27 of the salting table 26. Salting can be done in a mechanised manner or through manual application using a bucket or similar container containing a weighed quantity of salt that is spread as evenly as possible over the curd after all whey has been discharged. The curd could also or alternatively be placed in a container with brine.

Salting, which is not required for all cheese varieties and therefore may or may not be included in the method of the invention, typically adds flavour and acts as a preservative in the finished cheese. Syneresis continues after the commencement of salting in many cheese-making processes. An outlet 27 of the salting table 26, which may include e.g. drainage grooves or conduits feeding to the outlet 27, supplies the resulting salt whey as a salt whey stream 54. In this regard in the illustrated cheese-making method the salt whey is kept separate from the whey in silo 51, although in variants of the cheese-making process this need not necessarily be the case.

The finished curd is placed in cheese moulds of for example metal, wood or plastic, which determine the shape of the finished cheese. In some cheese-making processes, especially those relating to "hard" cheeses, the moulds bind and press the curd particles together. This step can be carried out at a block former 28. Block forming of cheese results in further syneresis. In block forming the curd and whey as stated are placed in moulds from where whey is further drained away via an outlet 29 of the block former 28. The whey drained via outlet 29 becomes part of the stream 54 of salt whey.

Following block forming the cheese is subjected to packaging and preserving steps as exemplified in a non-limiting manner in FIG. 1 through steps of wrapping/shrink film wrapping 56, cartoning 57, chilling 58 and palletising 59.

Figure 2:
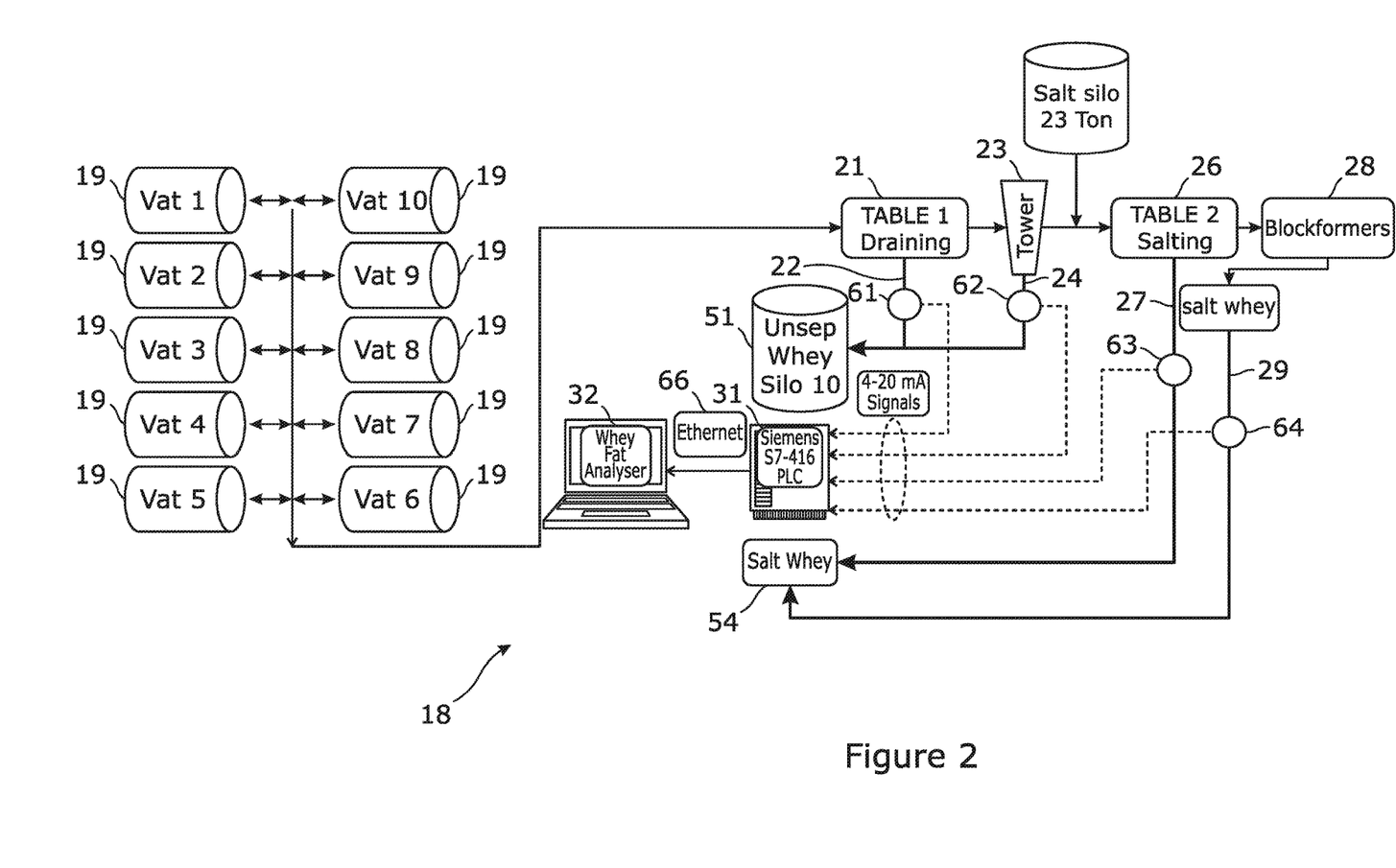
FIG. 2 shows a detail of part of the FIG. 1 apparatus, illustrating some possible sensor locations in accordance with the invention.

As best illustrated in FIG. 2, which shows part of the FIG. 1 apparatus in more detail, in accordance with the invention optical sensors 61, 62, 63, 64 measure the degree of occlusion and/or turbidity of the streams of whey leaving via the outlets 22, 24, 27 and 29 of the draining table 21, the cheddaring tower 23, the salting table 26 and the block former 28 respectively. FIG. 2 shows some possible locations of the optical sensors are to calculate whey fat losses, although numerous other locations are possible. Thus the invention is not limited to the illustrated locations and the sensors can take readings from other parts of a dairy product making apparatus that discharge a whey stream. More or fewer sensors than those illustrated may be provided. It is not necessary that every stream of whey in the cheese-making apparatus is provided with sensors as illustrated.

The sensors 61, 62, 63, 64 may be designed for installation directly into the dairy product lines at the whey stream outlets 22, 24, 27 and 29. Materials for making the sensors include Polypropylene, Polyvinylidene fluoride (PVDF) and stainless steel. The surfaces of the sensors may be coated with Radium. One example of a suitable sensor type is a Quadbeam™ S-series sensor available from LTH Electronics Ltd of Luton, Bedfordshire, UK. Such sensors may readily be installed in whey-conveying pipelines e.g. by piercing the pipes and creating screw threads in the resulting apertures; or by removing one or more screw-threaded plugs that may be present in process plant pipework and replacing the plugs with screw collars forming parts of the sensors.

Each optical sensor is in the preferred embodiment of the invention made up of at least two light sources and a corresponding number of light detectors, although other versions are possible. The two light sources can be infrared (IR) light emitting diodes and photo diodes which are pulsed in sequence, so as to generate light beams one alternating with the other. When the light sources and the light detectors are of the type indicated above they are set at exactly 90 degrees to each other. The light sources and detectors may also be set at other angles to each other, particularly if other sensor designs than those indicated are used.

During operation each light source is pulsed in sequence such that the sensor produces two detector currents, one from the detector opposite the light source (attenuation) and the other from the detector at 90 degrees (or other angle) to the light source (scattered light).

The sensors shine a light of known intensity at a fixed distance through a whey stream at the locations of the light detectors. When the frequency of the IR is the same as the vibrational frequency of a fat molecule bond, absorption of the IR occurs. The amount of IR absorbed corresponds to the amount of fat that is present. Each of the light detectors generates a current that indicates the attenuation and/or scattering of light in the stream of whey.

There are other ways that could be used for measuring the amount of fat in the whey streams and the invention is not limited to using IR spectroscopy as described.

The current values reflective of the attenuation and scattered light in the stream of whey are passed as signified by dotted lines in FIG. 2 to a processor 31 and the corresponding percentage fat ("whey fat % data") in the whey stream is calculated in real-time. The processor 31 runs a software application that takes the "whey fat % data" value as an input. Using the volumetric totals and the density factor of the whey fat, the "whey fat mass (Kg) per whey stream" is calculated. Further data analysis gives a "fat loss per vat" which is presented as a control chart to operators of the dairy product apparatus. The control chart can be used to determine whether the manufacturing process is in a state of statistical control.

The processor 31 in the illustrated embodiment of the invention transfers values, via wired technology such as an Ethernet 66 or using wireless technology, to a screen of e.g. a personal computer 32 to be displayed.

Figure 3:
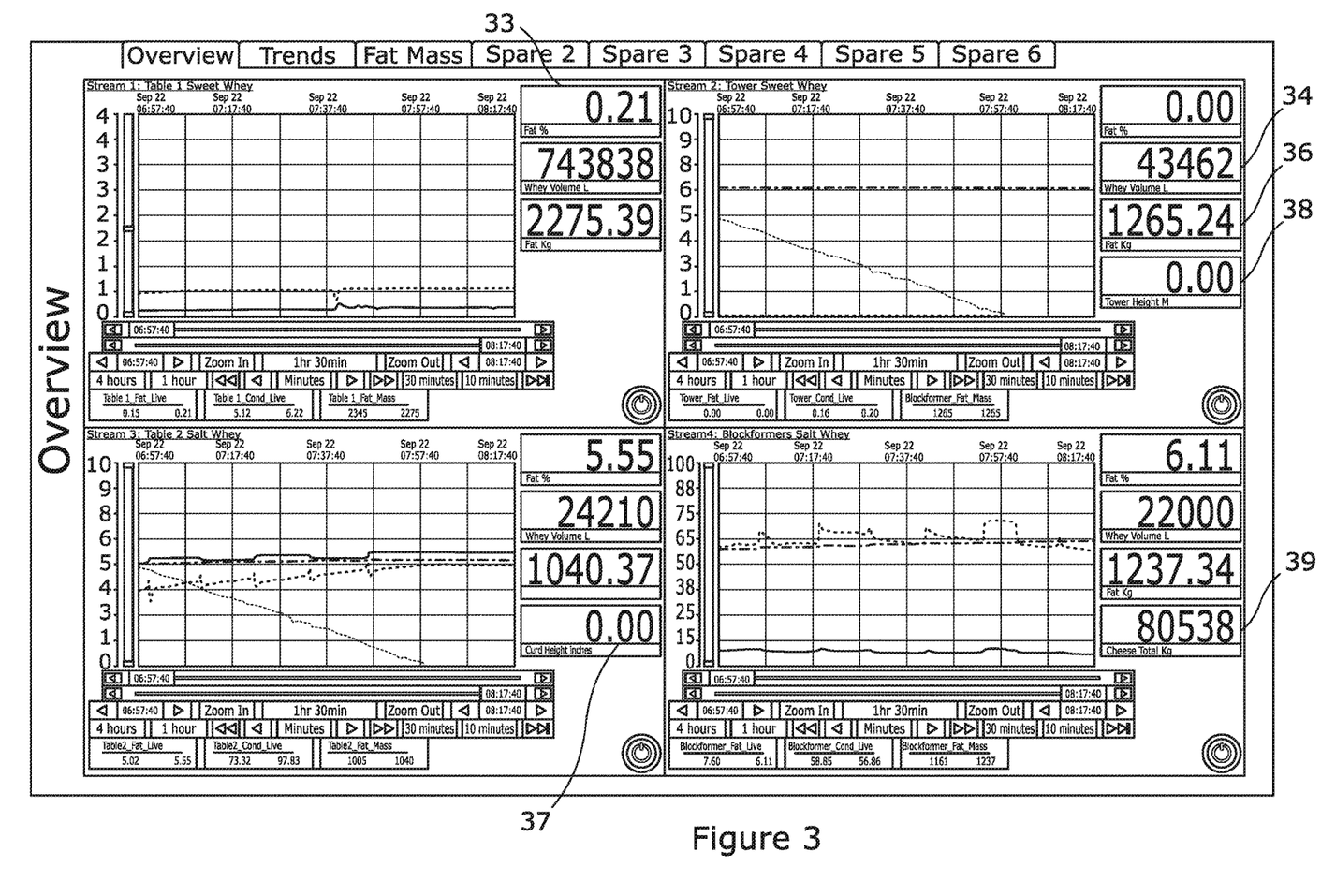
FIG. 3 is a sample view of a whey stream analysis carried out in the FIGS. 1 and 2 apparatus.

FIG. 3 is a resulting sample display view of a whey stream analysis deriving from a particular vat 19. Examples of values that are displayed are "fat %" 33, "whey volume" 34, "weight of fat (kg)" 36, "curd height" 37, "tower height" 38 and "total weight of cheese" 39. More or less information than that shown can be displayed. The various data can also be displayed in arrangements that differ from that illustrated in FIG. 3.

Statistical Process Control (SPC) limits are calculated and added to the control chart which alerts the operators if any given cheese vat is not following the specification required for producing the desired cheese. The control chart limits are automatically adapted and recalculated depending on the cheese recipe. The whey fat data are continuously read by the system and the amount by which the whey fat is out of specification is presented to the operators together with a calculated change to the recipe in order to compensate for the whey fat loss in the next production cycle corresponding to the next vat in sequence that is to be processed.

The processor 31 may take a variety of forms. Programmable line controller (PLC) devices, which are commonly encountered in the food processing and other automated manufacturing industries, are one class of processor that is suitable for use in apparatus according to the invention. An example of a PLC that potentially is suitable in this regard is the Siemens S7-416.

The processor 31 and/or the personal computer 32 may be programmed to perform the calculating steps of the method of the invention. In some embodiments of the invention it is not necessary to provide both a PLC and a personal computer. Numerous possible processor arrangements will be known to the person of skill in the art. It is however desirable that the processor arrangement includes at least one display device for displaying the results of the whey fat assessment to a human operator or supervisor of the production plant.

Figure 4:
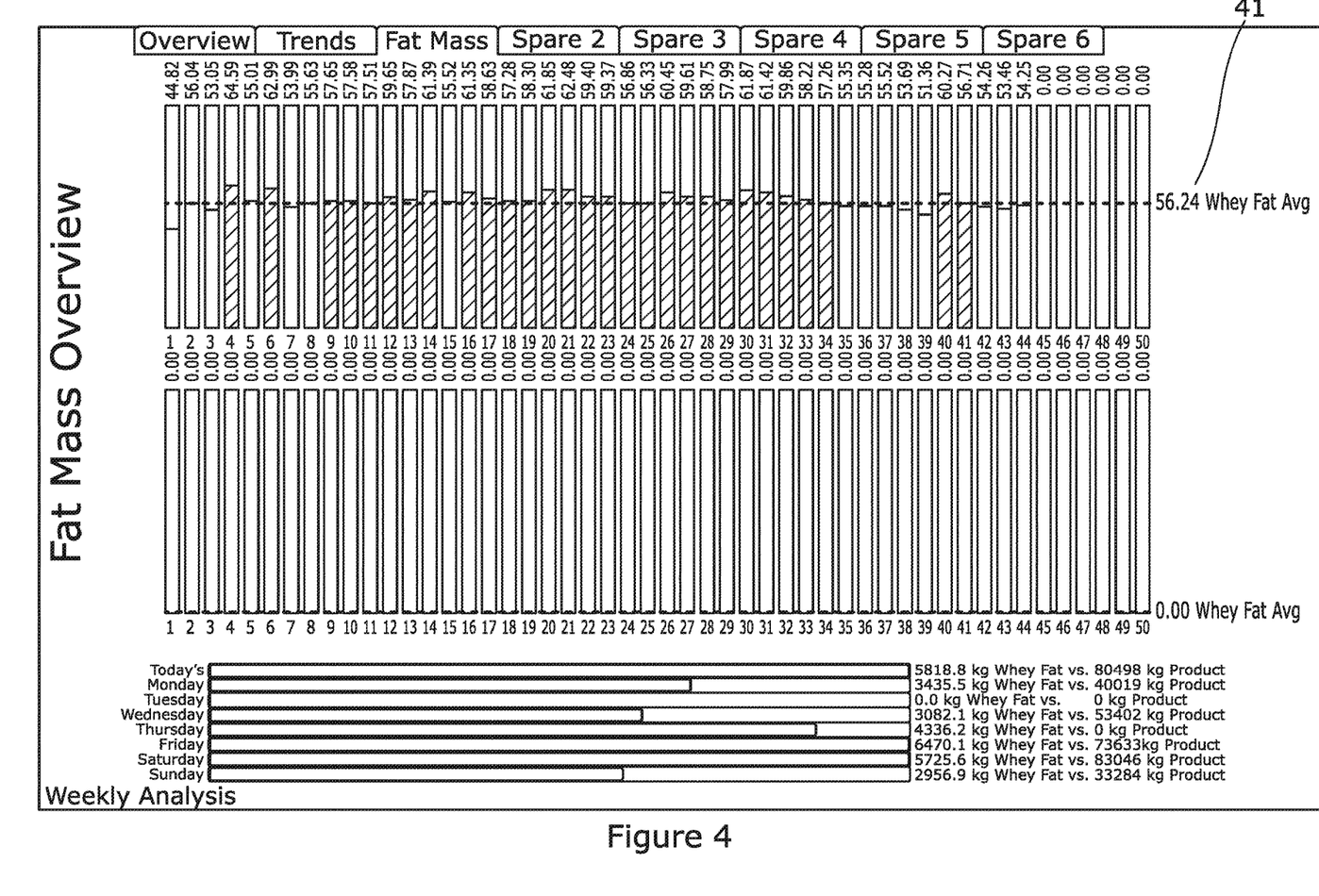
FIG. 4 is a sample view comparing the analysis of whey fat in different vats.

FIG. 4 shows a sample view comparing the analysis of whey fat in different vats 19 by way of a bar chart 40. Other types of charts and graphs may be used.

The horizontal axis of the bar chart indicates the Vat Number and the vertical axis displays the fat mass in the whey stream for a particular vat. A horizontal line 41 across the diagram indicates the average level of optimum fat that should be found in the whey. The horizontal line 41 assists an operator to determine which vat 19 should have its parameters adjusted, according to the fat mass values that rise above or fall below the horizontal line 41.

In a system of for example 10 vats, if Vat Number 3 is found to be out of specification by having say an extra 2 kg of whey fat, a command can be issued by the processor 31 for Vat Number 13 (i.e. the same vat, in the next succeeding process cycle) so as to effect adjustment of a parameter so that the value of fat loss lies within the predetermined range. An example of a parameter that can be adjusted in order to achieve this is the cutting speed of the curd.

Real-time analysis of the fat in whey therefore allows for adjustments to be carried out in the next cycle in sequence to compensate for the losses in the previous cycle.

The processor 31 is capable of issuing commands that adjust one or more of the parameters such that the value of specific fat loss lies within the predetermined range. Indicia corresponding to these commands can also be displayed.

The analysis of whey fat in the making of yogurt (to which the invention additionally pertains) is similar in certain aspects to the fat analysis in the making of cheese. For conciseness, apparatus parts and method steps that have been explained above for the making of cheese will not be repeated for the making of yogurt. The person of skill in the art will be aware of those process steps and apparatus items described above that are not required in yogurt making and therefore can be omitted or bypassed.

The making of yogurt requires fermentation of milk through the addition of starter cultures, such as *Lactobacillus bulgaricus* and *Streptococcus thermophilus*, to form a curd and whey mixture. To stop the fermentation process, before the yogurt curd becomes too hard, the mixture is cooled at a chosen point in the fermentation process.

The dairy product making apparatus for making yogurt comprises a drainer. The cooled mixture of yogurt curd and whey that may be formed in a vat that is similar to the vats 19 described above is placed on the drainer which removes moisture from the curd and whey mixture. The drainer contains screens that allow the whey to drain from an outlet, but which trap the curd. Other ways of trapping the curd and allowing the whey to be removed may be used in the method of the invention.

Optical sensors, as described above for assessing fat in whey in the making of cheese or adopting one or more other designs, may be installed at the drainer outlet for measuring the amount of fat in the whey. The current values that indicate the attenuation and/or scattered light in the stream of whey from the drainer outlet are passed to a processor for analysing the percentage fat in the whey in a similar or identical manner to that described above.

As noted herein the optical sensors 61, 62, 63, 64 (if all are present) and any further sensors that may be present may be constituted together with a processor such as but not limited to processor 31 and/or personal computer 32 as a portable kit or unit. This may be largely contained within e.g. an instrument housing, with the sensors connected e.g. using trailing leads whereby to facilitate their insertion into the whey streams as described. Such portable apparatus may be permanently or temporarily connected to measure fat levels in a particular set of whey streams. The apparatus of the invention lends itself to retrofitting in existing cheese-making lines, although it may equally be installed at the time of building a manufacturing plant.

The invention allows real-time analysis of whey fat loss which provides useful information influencing any necessary adjustments in the dairy product making process. This helps to optimise the amount of fat being retained in the dairy product. Overall the method and apparatuses of the invention represent highly useful improvements in dairy processing activities.

Preferences and options for a given aspect, feature or parameter of the invention should, unless the context indicates otherwise, be regarded as having been disclosed in combination with any and all preferences and options for all other aspects, features and parameters of the invention.

The listing or discussion of an apparently prior published apparatus in this specification should not necessarily be taken as an acknowledgement that the apparatus is part of the state of the art or is common general knowledge.

The invention claimed is:

1. A method of assessing fat in whey in the making of a dairy product in accordance with a dairy product recipe, the method comprising the steps of:
   a. using one or more optical sensors to sense at least one stream of whey separated from curd in dairy product making apparatus and generate one or more signals indicative of the degree of occlusion of the stream of whey;
   b. converting or processing one or more said signals as a measure of the specific mass of fat lost from curd in a dairy product-making plant into the stream of whey;
   c. assessing whether the value of specific mass of fat lost obtained in Step b lies within or outside a predetermined fat loss range; and
   d. if the said value of specific mass of fat lost is outside the predetermined range, adjusting the recipe so that the value of specific mass of fat lost lies within the predetermined range.

2. A method according to claim 1 wherein the dairy product is cheese or yogurt.

3. A method according to claim 1 wherein the dairy product is butter.

4. A method according to claim 1 including the steps of:
   e. using a plurality of optical sensors to sense a corresponding plurality of streams of whey separated from curd in dairy product making apparatus and generate a corresponding plurality of signals respectively indicative of the degree of occlusion of the streams of whey;
   f. converting or processing the said signals as measures of the specific mass of fat lost from curd in the dairy product making plant in the streams of whey;
   g. assessing whether the values of specific mass of fat lost obtained in Step f lie within or outside corresponding predetermined fat loss ranges; and
   h. if one or more said values of specific mass of fat lost is outside a said corresponding predetermined range, adjusting the recipe so that each value of specific mass of fat lost lies within the corresponding predetermined range.

5. A method according to claim 1 wherein the dairy product is cheese or yogurt and including the steps of:
   e. using a plurality of optical sensors to sense a corresponding plurality of streams of whey separated from curd in dairy product making apparatus and generate a corresponding plurality of signals respectively indicative of the degree of occlusion of the streams of whey;
   f. converting or processing the said signals as measures of the specific mass of fat lost from curd in the dairy product making plant in the streams of whey;
   g. assessing whether the values of specific mass of fat lost obtained in Step f lie within or outside corresponding predetermined fat loss ranges; and
   h. if one or more said values of specific mass of fat lost is outside a said corresponding predetermined range, adjusting the recipe so that each value of specific mass of fat lost lies within the corresponding predetermined range
   wherein the plurality of optical sensors sense streams of whey respectively at one or more of (i) an outlet of a draining table of the dairy product making apparatus; (ii) an outlet of a cheddaring tower of the dairy product making apparatus; (iii) an outlet of a salting table of the dairy product making apparatus; and
   (iv) an outlet of a block former of the dairy product making apparatus.

6. A method according to claim 1 including the steps of:
   e. using a plurality of optical sensors to sense a corresponding plurality of streams of whey separated from curd in dairy product making apparatus and generate a corresponding plurality of signals respectively indicative of the degree of occlusion of the streams of whey;
   f. converting or processing the said signals as measures of the specific mass of fat lost from curd in the dairy product making plant in the streams of whey;
   g. assessing whether the values of specific mass of fat lost obtained in Step f lie within or outside corresponding predetermined fat loss ranges; and
   h. if one or more said values of specific mass of fat lost is outside a said corresponding predetermined range, adjusting the recipe so that each value of specific mass of fat lost lies within the corresponding predetermined range and
   wherein one or more optical sensors sense one or more streams of whey at an outlet of a drainer or strainer of the dairy product making apparatus.

7. A method according to claim 1 wherein the or each stream of whey is/are generated from ingredients in a plurality of vats forming part of the dairy product making apparatus used sequentially to provide curds and whey.

8. A method according to claim 1 wherein the step of generating one or more signals indicative of the degree of occlusion of the at least one stream of whey includes generating one or more signals indicative of the degree of turbidity of the at least one stream of whey.

9. A method according to claim 1 wherein the step of using one or more optical sensors to sense at least one stream of whey includes directing a light beam from at least one light source through a said stream of whey towards an associated light detector that generates a current in dependence on the attenuation of the light in the stream of whey.

10. A method according to claim 1 wherein the step of using one or more optical sensors to sense at least one stream of whey includes directing a light beam from at least one light source through a said stream of whey towards an associated light detector that generates a current in dependence on the attenuation of the light in the stream of whey and wherein the step of using one or more optical sensors to sense at least one stream of whey includes directing a respective light beam from each of at least two light sources through a said stream of whey towards respective associated light detectors that generate currents in dependence on the attenuation of the light in the stream of whey.

11. A method according to claim 10 wherein the step of using one or more optical sensors to sense at least one stream of whey includes directing a light beam from at least one light source through a said stream of whey towards an associated light detector that generates a current in dependence on the attenuation of the light in the stream of whey, wherein the step of using one or more optical sensors to sense at least one stream of whey includes directing a respective light beam from each of at least two light sources through a said stream of whey towards respective associated light detectors that generate currents in dependence on the attenuation of the light in the stream of whey and wherein the two light sources are each intermittent and generate light one alternating with the other.

12. A method according to claim 1 further including the step of displaying via a display device one or more indicia indicative of the value of specific fat loss.

13. A method according to claim 1 including generating, based on the measure of the specific fat loss in the or each stream of whey, one or more commands that effect adjustment of a parameter of dairy product making apparatus so that the value of specific fat loss lies within the predetermined range.

14. A method according to claim 1 including the step of storing a plurality of recipes in a relational database together with a plurality of predetermined ranges of specific fat loss value, the method further including the steps of selecting a said recipe; associating a said range of specific fat loss value with the selected recipe; and generating the or each said command based on the specific fat loss value associated with the recipe.

15. Dairy product-making apparatus for carrying out a method according to claim 1 including one or more ingredient vats for containing dairy product making ingredients; at least one drainer having an outlet permitting removal of one or more streams of whey separated from curd; one or more optical sensors for sensing the one or more said streams of whey and generating one or more signals indicative of the degree of its occlusion; and a processor for converting one or more said signals as a measure of the specific mass of fat lost from curd into the stream of whey.

16. Apparatus according to claim 15 wherein the drainer is selected from the list including a draining table and a strainer.

17. Apparatus according to claim 15 wherein the drainer is selected from the list including a draining table and a strainer and additionally comprising a cheddaring tower, a salting table and a block former the mutual relationship of which permits the making of dairy product.

18. Apparatus according to claim 15 wherein the or each optical sensor includes at least two light sources that direct light through a said stream of whey and a corresponding number of respective associated light detectors that receive the light and generate currents in dependence on the attenuation of the light in the stream of whey.

19. Apparatus according to claim 15 wherein the or each optical sensor includes at least two light sources that direct light through a said stream of whey and a corresponding number of respective associated light detectors that receive the light and generate currents in dependence on the attenuation of the light in the stream of whey and wherein the at least two light sources each generate light intermittently in alternation one with the other.

20. Whey stream fat measuring apparatus comprising one or more sensors for sensing one or more streams of whey and generating one or more signals indicative of its degree of occlusion; and a processor for converting one or more said signals as a measure of the specific mass of fat lost from curd into the stream of whey.

21. Apparatus according to claim 20 wherein the or each optical sensor includes at least two light sources that direct light through a said stream of whey and a corresponding number of respective associated light detectors that receive the light and generate currents in dependence on the attenuation of the light in the stream of whey.

22. Apparatus according to claim 20 wherein the or each optical sensor includes at least two light sources that direct light through a said stream of whey and a corresponding number of respective associated light detectors that receive the light and generate currents in dependence on the attenuation of the light in the stream of whey and wherein the at least two light sources each generate light intermittently in alternation one with the other.

23. Apparatus according to claim 20 that is humanly portable and releasably connectable to sense one or more streams of whey in dairy product-making apparatus.

* * * * *